United States Patent [19]

Seitz, Jr.

[11] Patent Number: 4,824,434

[45] Date of Patent: Apr. 25, 1989

[54] APPARATUS USED IN A METHOD FOR REMOVING TISSUE AND LIVING ORGANISMS FROM HUMAN BODY CAVITIES

[76] Inventor: H. Michael Seitz, Jr., 214 Airdale Rd., Rosemont, Pa. 19010

[21] Appl. No.: 135,701

[22] Filed: Dec. 21, 1987

Related U.S. Application Data

[63] Continuation-in-part of Ser. No. 3,133, Jan. 14, 1987, Pat. No. 4,731,052.

[51] Int. Cl.[4] .............................................. A61M 1/00
[52] U.S. Cl. ......................................... 604/27; 600/33
[58] Field of Search .................. 604/27, 29, 28, 30, 604/32-35, 43, 44, 317, 319, 320, 323; 600/33-35

[56] References Cited

U.S. PATENT DOCUMENTS 3,081,770 4/1963 Hunter .................................. 604/33
4,334,538 6/1982 John ...................................... 604/35

FOREIGN PATENT DOCUMENTS 1019560 2/1966 United Kingdom ................... 604/35

Primary Examiner—C. Fred Rosenbaum
Assistant Examiner—J. L. Kruter
Attorney, Agent, or Firm—Austin R. Miller

[57] ABSTRACT

This invention provides an improved aspirating and flushing device designed for use in in vitro fertilization procedures in which eggs are delicately removed from the human ovary without need for open surgery. Although the device is intended for one-time use only, a permanent, interchangable stainless steel suction valve assembly can be substituted for the disposable valve if desired. The present invention is adaptable for both trans-abdominal laparoscopic procedures, as well as a trans-vaginal procedure that is performed with the aid of ultrasonagraphy.

10 Claims, 9 Drawing Sheets

APPARATUS USED IN A METHOD FOR REMOVING TISSUE AND LIVING ORGANISMS FROM HUMAN BODY CAVITIES

CROSS REFERENCE TO RELATED APPLICATION

This application is a continuation-in-part of U.S. patent application Ser. No. 3,133, filed Jan. 14, 1987 now U.S. Pat. No. 4,731,052.

BACKGROUND OF INVENTION

This invention relates generally to an improved aspirating and flushing surgical device and method designed to safely and efficaciously remove fluid, tissue and minute living organisms from within enclosed human body cavities. Specifically, this invention and its embodiments relate to an infertility procedure and apparatus whereby human eggs (ova) are surgically removed from the female ovary for use in in vitro fertilization (IVF) procedures.

FIELD OF INVENTION

IVF is a recent approach to human infertility that has enabled countless couples to have children which would otherwise be unlikely or impossible. IVF entails surgical removal of human eggs at a precise time during the female menstrual cycle and transporting them in appropriate mediums to a laboratory where they are artificially inseminated in a glass dish with the husband's spermatazoa. After remaining in a precise laboratory environment for a fixed amount of time, the ova are examined for evidence of early fertilization. Eggs displaying definite signs of normal fertilization (embryos) are placed into the uterine cavity, preferably through a fine catheter for possible implantation and pregnancy. Transfer of embryos is performed about 48 hours after the unfertilized eggs are retrieved from the ovary. The current success rate of this procedure is variously reported to be between 15 and 20%.

There are three primary methods employed for the purpose of human egg retrieval. The method of retrieval is determined by multiple factors including the type and extent of the disease alleged to be responsible for infertility. Most major IVF centers prefer a trans-vaginal-approach which utilizes a cylindrical ultrasound vaginal probe. An ultrasound transducer is located in the distal end of an ultrasound cylindrical probe. When the unit is placed deeply into the vagina, it enables the operator to view the intra-abdominal contents on a nearby ultrasound screen. The probe is designed to accomodate a stainless steel needle guide which can be fixed in place to the probe.

When performing IVF ovum recovery, an aspirating needle is inserted into the needle guide and then placed deeply into the vagina. The direction and position of the needle are observed and followed ultrasonically on the ultrasound monitoring screen. In this procedure the needle need only penetrate the thin vaginal wall in order to gain access into the abdominal cavity. Insufflation of the abdominal cavity with carbon dioxide gas is not necessary in this procedure. Ovarian follicles, which contain human eggs, are easily identified on the ultrasound screen and, in experienced hands, puncture and aspiration of these follicles become relatively simple tasks.

At the same time as entry of the aspirating needle into the ovarian follicle, the surgeon activates apparatus providing vacuum pressure, which assists in delivering the contents of the follicle, including the egg, into a collecting vessel. Irrigation of the follicle is frequently necessary if the egg is not retrieved in the initial aspirate. This method of ovum retrieval has gained in popularity because it can be performed in an out-patient setting under local anesthesia and, because it is less traumatizing, requires less post-operative recovery time.

In some instances ovum retrieval cannot be performed by the ultrasound method. In such cases this can be effectively performed trans-abdominally by introduction of an intra-abdominal viewing means (laparoscope). In this procedure the egg containing follicle can be clearly viewed, and aspiration of the follicle can be performed under direct vision. In order to perform the procedure safely and provide operative visibility, it is important that the abdominal cavity be distended with carbon dioxide gas prior to placement of any intra-abdominal instruments. The laparoscope is introduced through a small incision in the area of the navel. A second and third small puncture site are made to accomodate introduction of the aspirating needle and grasping forceps, which is necessary to stabilize the ovary for folliclar penetration. Although this type of ovum recovery is used frequently, it has the disadvantage of requiring a general anesthetic and, therefore, contributes to a prolonged patient recovery time.

A third method of IVF ovum recovery has gained more attention due to an alleged higher success rate. This procedure, known as Gamete Intrafallopian Transfer (GIFT), utilizes the trans-abdominal laproscopic technique and incorporates ovum recovery and sperm-egg transfer in the same operation. Eggs are retrieved in the usual fashion, taken to the laboratory where they are inseminated in vitro and returned to the operating room where a mixture of sperm and egg are deposited into the fallopian tube, preferably through a fine catheter. In this procedure, eggs are not fertilized in vitro before transfer to the patient, but are placed into the Fallopian Tube along with spermatazoa to become fertilized in a natural environment. In all other IVF procedures, eggs are fertilized in vitro and allowed to become embryos before placement into the uterine cavity.

In systems requiring aspiration of fluid and/or tissue through a closed airtight tubular device, it is necessary to utilize a vacuum source in order to create suction. This has been done manually with a large hypodermic syringe, supplied through a central mechanical source available in most hospital units, or with a compact floor model vacuum pump commercially available. It is important that the force of this suction can be measured and accurately controlled. In delicate operations such as in IVF egg recovery, it is of paramount importance to have suction actuated by the surgeon when attempting to retrieve a human egg. It is quite important that suction be applied at the precise moment the compartment containing the egg (follicle) is punctured with the aspirating device. It has been found that delegating the activation of suction to another person is frequently undesirable and unworkable.

The compartment that houses the human egg is a fluid filled structure which is under pressure, and if puncture of the structure is made asynchronously upon the activation of suction, the follicle contents escape and the egg contained within is frequently not recovered. This is particularly true when the vaginal ultrasound method of ovum retrieval is utilized. It has been found that current apparatus is limited in capability because of its lack of capacity to easily and quickly shift from a suction mode, to no operation, to a flushing mode and back to a suction mode. This quick shifting of modes requires a quick reaction from the operating surgeon. Some clinics favor use of a foot pedal vacuum control mechanism located on the floor in the vicinity of the operating surgeon. Many have found this method to be cumbersome, expensive and subject to malfunction. Because it is highly desirable that the surgeon personally actuate the suction, it is preferred that the aspiration control device be designed to require as little conscious thought as possible to manipulate and not to be contrary to natural movement.

In addition to aspirating, some situations require introduction of a washing or flushing solution into the exact location where aspiration has occurred without re-entry of the aspirating needle. It is desirable for a flushing solution to be introduced into the same point of aspirating after aspiration has occurred in order to redistend or refill the evacuated compartment (follicle) so that a second attempt at recovery of the egg can be made without additional puncture of the follicle. Frequently the egg is not removed at the time of initial aspiration, but is recovered in subsequent washings. The human egg is enveloped in many layers of cells (cumulus) which are extremely important to the nourishment, growth and development of the egg and should not be removed or destroyed. Excessive vacuum pressure tends to damage the eggs. The inner diameter of the aspirating and collecting system is extremely important. If this diameter is too small, the eggs can easily be divested of vital cumulus cells surrounding and protecting the eggs, which tends to diminish the success of the procedure. Moreover, a small inner diameter tends to increase the speed of passage of the aspirated contents and creates the potential for physical injury to the egg. On the other hand, if the outer diameter of the aspirating needle is too large, the risk of trauma induced complications is increased. It is for this reason that concentric needle systems are undesirable.

A comparative analysis of the laparoscopic and ultrasonic vaginal ovum retrieval methods indicated a major deficiency inherent in aspirating systems designed for the purpose of trans-vaginal ultrasound ovum recovery. This deficiency will hereinafter be referred to as "deadspace." This term has reference to residual fluid and follicular contents that remain in the collecting system and fail to reach the collecting vessel despite complete evacuation of the ovarian follicle. This volume can be substantial and is directly proportionate to the length of the aspirating needle, the functional inside diameter of the aspirating needle, as well as the distance between the collecting vessel and the proximal end of the aspirating needle. It should be remembered that in performing vaginal ultrasound ovum recovery, abdominal insufflation of carbon dioxide gas is not utilized and gas cannot be used to clear the aspirating system. Moreover, once the follicle is penetrated, removal of the needle is undesirable as it favors further loss of fluid and follicular contents, as well as additional trauma when re-entry of the follicle becomes necessary.

When performing an ovum retrieval trans-abdominally with the laparoscope, follicular penetration and collapse can be clearly seen and all one needs to do to clear the system is to remove the needle from within the follicle momentarily and the carbon dioxide gas used to insuflate the abdominal cavity will insure the flow of follicular fluid and contents into the collecting vessel. Under direct vision, the needle can be carefully reinserted in to the original puncture site and proceed to redistend the follicle with washing fluid, if necessary. The problem of "dead-space," therefore, exists only in those systems designed for trans-vaginal ovum recovery. This is a major deficiency that has remained unsolved in prior methods and apparatus for this purpose.

DESCRIPTION OF THE PRIOR ART

U.S. Pat. No. 4,299,221 discloses an irrigation and suction handpiece having three separate passageways, one each for pressurized air, vacuum suction and an irrigant liquid. The passageways for the vacuum suction and an irrigant extend to the target area, while the pressurized air passageway terminates short of the target. A valve means is provided on the handpiece for the irrigant.

This device is undesirable for delicate surgical techniques for several reasons. There are separate passageways for aspiration and flushing which is overly traumatic for a small target. The passageways do not terminate at the same point, which requires unwanted needle manipulation when shifting from an aspiration mode to a flushing mode. Also, there is no valve to control aspiration on the device itself. Having such a valve is highly preferred for direct surgeon's control.

U.S. Pat. No. 4,493,694 discloses a surgical preaspirator, which supplies an irrigation fluid by way of an outer concentric passageway to the end of an inner concentric passageway to assist in aspirating through the inner concentric passageway various body tissues.

However, this device does not have a valve to control aspiration located thereon, and it does not introduce irrigant into the target area. Irrigation fluid does not travel outside of the device to flush the target, but instead, assists the aspirated tissues along the suction passageway.

U.S. Pat. No. 4,526,573 discloses suction-irrigation equipment with a control valve. The device has parallel bores, one connected to a vacuum source and the other to an irrigating fluid. A valve assembly having two inlet conduits is attached to the bores, one inlet to the suction bore and one inlet to the irrigation bore. An outlet conduit can be connected to one or the other of the bores by displacing a valve member.

While the device is disclosed as having a neutral position with no suction or irrigation, the valve member should be precisely placed in order to establish the neutral position, and the operator should maintain the position, or the spring actuated valve member will automatically displace it to the suction mode. This runs counter to the optimal arrangement of producing aspiration upon shifting or depressing the valve member, and is therefore undesirable.

The internal design of the valve assembly is such that it tends to subject the aspirated tissue and fluid to transversing sharp corners and much turbulence. There is also the possibility that if the valve member is moved as the tissue passes through the valve chamber that it could be caught in the valve member flanges, and either be damaged, crushed or permanently caught within.

In some cases, surgeons have used a simple hypodermic syringe placed directly onto the hub of the aspiration needle. This technique is inconvenient and highly undesirable due to the almost consistent loss of aspirate that occurs when hypodermic syringes are removed and added. In addition, excessive negative pressures are produced with standard hypodermic syringes, which subject the egg and follicular contents to risk of physical damage.

OBJECTS OF THE INVENTION

Thus, it is an object of the present invention to provide a disposable and semi-disposable aspirating and flushing device for use in a method which allows a surgeon to personally control aspiration through a valve located on the body of the hand-held device, which valve permits aspiration when depressed by the surgeon and interrupts aspiration upon release.

It is another object of the present invention to provide an aspirating and flushing device that permits aspiration, as well as providing a means for the introduction of a fluid for the purpose of refilling or flushing the cavity previously aspirated through the same single hollow needle used to penetrate the cavity (follicle).

It is an important object of the present to provide an interchangable aspirating needle designed to minimize the problem of "dead-space" within the aspirating needle when the device is adapted for transvaginal ultrasound procedures.

It is another important object of the present invention to provide a body member that can reduce the distance aspirated fluids and tissues are required to travel in order to reach the collecting vessel.

It is an important object of the present invention to provide an aspirating and flushing device for use in a method to pierce a follicle in a human female ovary and retrieve an egg therefrom for artificial insemination, with the internal design of the device being so constructed to provide a clear passageway for the egg to travel without obstruction or turbulence so that the egg is not lost, damaged or destroyed.

It is an important object of the present invention to provide an aspiration and flushing device which can quickly and easily be connected to an existing vacuum source and can handily be assembled for one-time use, thereby further reducing the element of infectious disease potential.

It is another object of the present invention to provide an aspirating and flushing apparatus in which all integral parts are interchangable and which facilitates rapid needle exchange during the procedure.

It is still a further object of the present invention to provide a special cannula-trocar extension in which application of a vacuum is utilized to provide introduction of the device into the body cavity and serve as a holding or grasping means when suction is applied to the main body of the device in order to grasp or hold tissues, remove excess blood and fluid from a cavity, as well as provide a portal of entry through which specialized surgical instruments can be introduced.

Another object of the present invention is to provide a re-usable stainless steel valve assembly which can be surgically sterilized with high heat and substituted for the disposable valve assembly if desired.

Other objects and advantages of the present invention and its embodiments will become readily apparent to those skilled in the art by a reading of the following description of the drawings, detailed descriptions of the preferred embodiments and the appended claims.

SUMMARY OF THE INVENTION

The present invention provides a disposable and semi-disposable aspirating and flushing device adaptable for the trans-abdominal and/or trans-vaginal recovery of eggs from the human ovary without open surgery for use in IVF procedures.

The surgeon's aspirating and flushing device has a first body with a needle extending therefrom for insertion into the human ovary for removal of an egg and for instruction of flushing fluid. The first body, or hub of the aspirating needle is constructed to contain a chamber into which the proximal end of the aspirating needle terminates. In addition, there is an exit or flushing portal extending outwardly from the chamber, which serves as a passageway through which fluid can be introduced into the system when required.

There is a second body that is fixed to the first body in an airtight fashion preferably utilizing a silastic O-ring. The second body contains a flexible tubing connectable to a vacuum means which extends into the flushing chamber and surrounds the distal end of the aspirating needle without contacting it. The flexible tubing surrounding the needle is of slightly greater inside diameter than the outside diameter of the needle and, therefore, creates an umbrella effect. This break in the continuity of the system allows flushing fluid to enter the aspirating needle and onto the target area (ovarian follicle).

The second body also contains a disposable or pinching valve assembly through which the flexible tubing passes. Depression of this valve allows suction through the flexible tubing and the needle for evacuation of the ovarian follicle and, when released, pinches the flexible tubing, thereby preventing suction and allowing flushing fluid to be introduced. When flushing is performed, the flushing portal is open while the aspirating valve is in the off or closed position and, when aspiration is performed, the flushing portal is closed. When the flushing portal is closed, the collecting vessel secured, and suction is activated, tissue and fluid being aspirated flow directly through the flexible tubing into a collecting vessel where the contents of the aspirate are retrieved. When performing this procedure trans-abdominally, the collecting vessel can be distant from the device. The terminal portion of the second body is constructed to permit rapid changing of needles and when fitted into a special cannula can serve as a suction holding device when the GIFT procedure is employed. This device is ideally suited for use in trans-abdominal laparoscopic methods of egg retrieval.

Other aspects of the present invention consist of placement of an airtight jacket loosely surrounding the main aspirating needle. This jacket is secured to the plastic needle hub and communicates with the flushing chamber. The jacket encloses all but the distal three inches of the aspirating needle where it is secured in an airtight fashion. The terminal portion of the aspiration needle surrounded by the airtight plastic jacket contains several small fenestrations so that fluid introduced at the exit or flushing portal will enter the chamber, traverse the space between the jacket and the aspirating needle, enter the distal portion of the aspirating needle through the fenestrations and exit at the site of needle penetration. During this flushing maneuver, with the aspirating needle in the off position, a slight amount of flushing fluid flows in the opposite direction until adequate back pressure is established. The collecting vessel is locked onto the device during the flushing step.

Another aspect of the present invention permits relocation of the collecting vessel onto the main body of the aspirating device, thereby further minimizing "deadspace" potential. This is accomplished by interposing a coupling mechanism between the needle hub and the valve assembly and serves as a means for attaching the collecting vessel directly onto the device. With the coupling mechanism in place, and aspiration being performed, aspirate flows directly into the collecting vessel rather than traversing the flexible tubing to a distant collecting site. This extension of the present invention substantially reduces "dead-space" while still providing an optimum diameter needle for penetration of tissue.

The semi-disposable unit possesses all advantages of the disposable unit and is of similar construction with the exception of a permanent stainless steel suction control valve assembly which can easily be disassembled, cleansed and assembled for high heat surgical sterilization. When the permanent control valve is utilized, the remainder of the aspirating-flushing device is discarded after one-time use while the valve assembly can safely be sterilized and re-used.

DETAILED DESCRIPTION OF THE DRAWINGS

Figure 1:
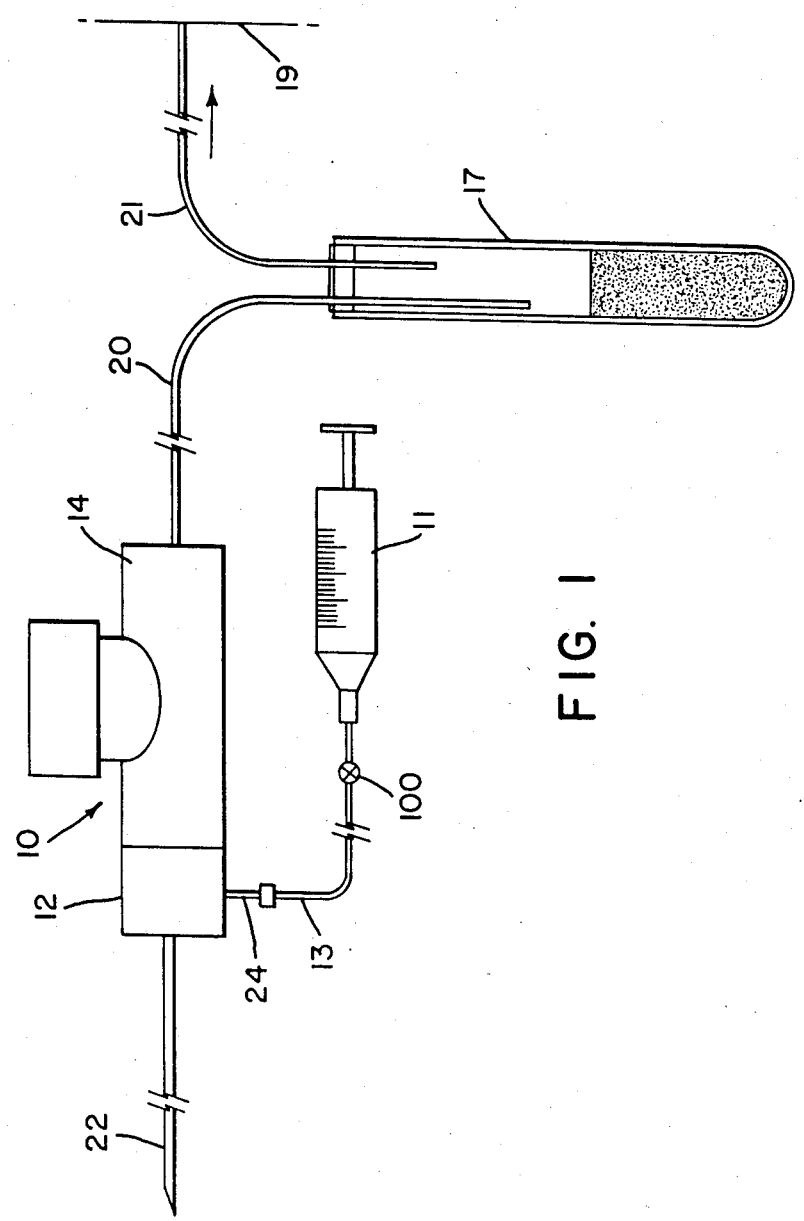
FIG. 1 is a schematic view of a system of apparatus for removing tissues, fluid and eggs in accordance with the present invention.

An apparatus for collecting human eggs in accordance with the method of the invention is shown in FIG. 1. Device 10 comprises primarily a first body portion 12 and a second body portion 14. Pointed needle 22, for insertion into a human body, connects to first body portion 12. Syringe 11, for the introduction of flushing fluid, connects to first body portion 12 at syringe portal 24 by way of flexible tubing 13. Flexible tubing 13 is provided with valve 100. Flexible tubing 20 exits second body portion 14 and connects to collection trap 17, which in turn is connected to a continuous vacuum source (not shown) in wall 19 by way of flexible tubing 21.

Figure 2:
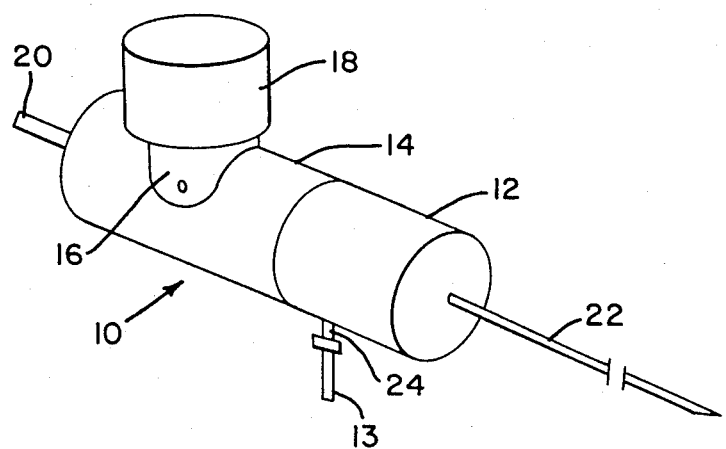
FIG. 2 is a plan view in perspective of one embodiment of an aspiration and flushing device in accordance with the present invention.

An aspiration and flushing device 10 designed for laparoscopic egg retrieval, is shown in FIG. 2. Device 10 has a first body portion 12 and a second body portion 14 Extending from second body portion 14 is a valve 16 having lever 18. Also extending from second body portion 14 is flexible tubing 20. First body portion 12 has a needle 22 extending outwardly from one end, and a syringe portal 24 at the side, with flexible tubing 13 extending therefrom.

Figure 3:
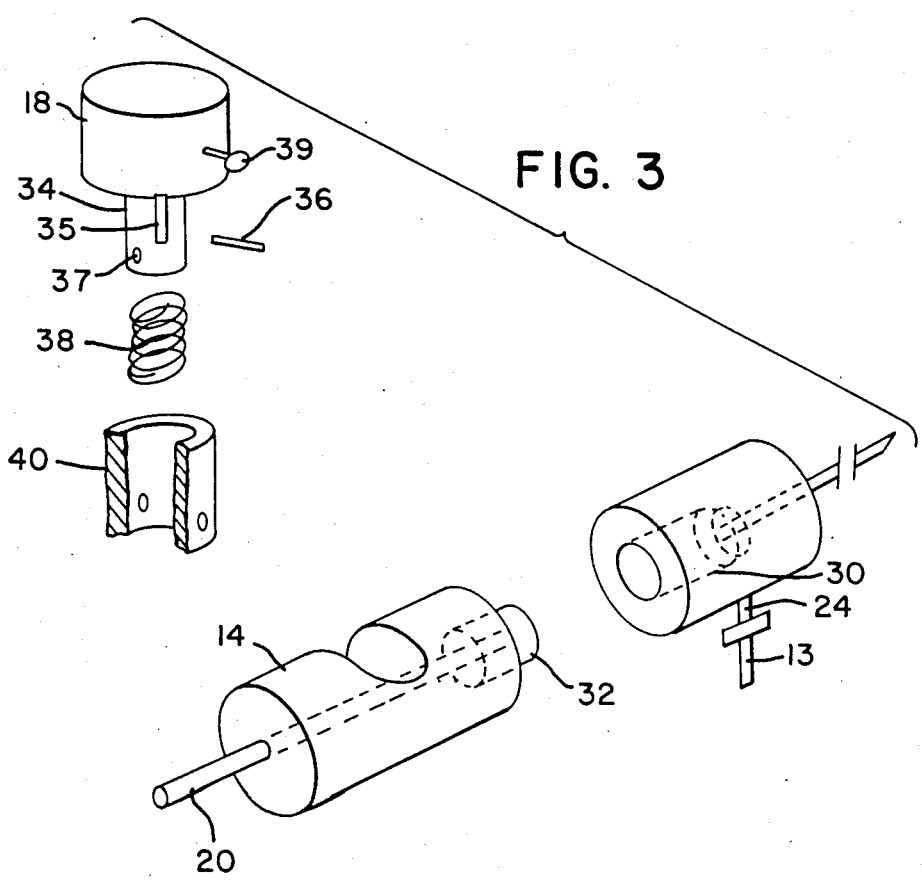
FIG. 3 shows a perspective view of one embodiment of the present invention, broken apart for ease of understanding.

First body portion 12 is shown broken away from second body portion 14 in FIG. 3. Dashed lines define a flushing fluid chamber 30 in first body portion 12. Needle 22 and a syringe portal 24 extend outwardly from first body portion 12. Flexible tube 20 extends outwardly from second body portion 14, and also extends interiorly through its length as defined by dashed lines. Extension 32 extends outwardly from the other end of second body portion 14.

Valve lever 18 has a downwardly extending plunger 34 with a slot 35 through which pinching pin 36 extends and a hole 37 to receive tubing 20. Spring 38 surrounds plunger 34 and is in turn surrounded by valve housing 40. Locking pin 39 selectively locks valve lever 18 to valve housing 40.

Figure 4:
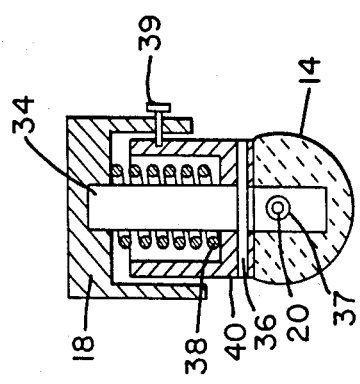
FIG. 4 is an end view of an aspiration and flushing device shown in section along the valve housing from FIG. 2, with the valve in the "on" position.

FIG. 4 shows lever 18 of second body portion 14 in a depressed position and being locked in place by lock pin 39, with spring 38 being compressed inside housing 40. Plunger 34 is similarly fully depressed with tubing 20 extending therethrough by way of hole 37. Pinching pin 36 is fixed within housing 40.

Figure 5:
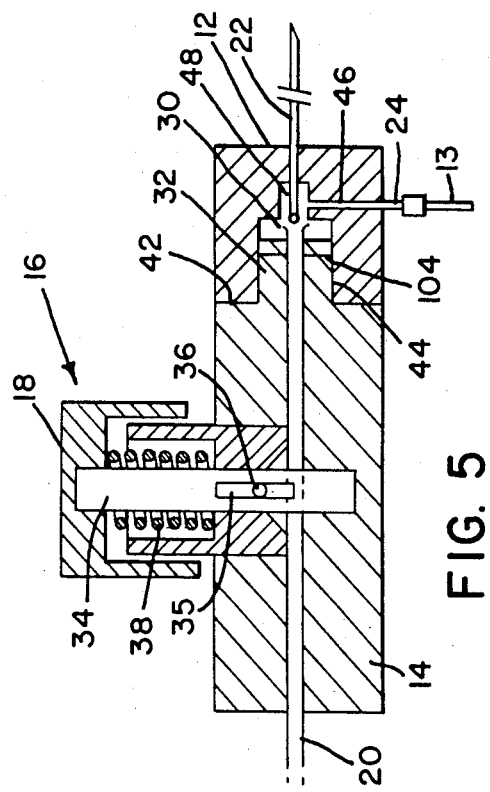
FIG. 5 shows a side sectional view of an aspiration and flushing device in accordance with the present invention with the valve in the "on" position.

FIG. 5 shows valve 16 similarly disposed as in FIG. 4. Lever 18 and plunger 34 are depressed, with spring 38 being compressed. Pinching pin 36 extends through slot 35 and is adjacent tubing 20 which extends through hole 37 (see FIG. 4).

First body portion 12 and second body portion 14 are connected together at end surface 42 and cylindrical surface 44 of extension 32. Extension 32 extends into first body portion 12 and forms flushing fluid chamber 30. O-ring 104 extends around extension 32. Tubing 20 extends into fluid flushing chamber 30 and surrounds a portion of the end of needle 22 which also extends into fluid flushing chamber 30. Syringe portal 24 connects fluid passageway 46 which connects into a portion 48 of fluid flushing chamber 30.

Figure 6:
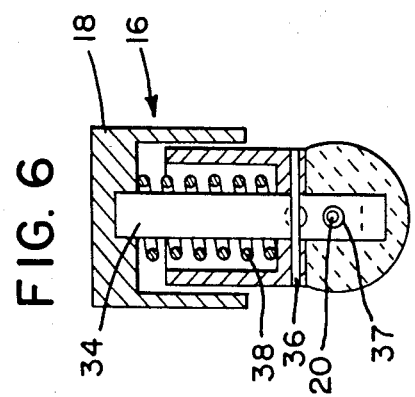
FIG. 6 is an end sectional view of the apparatus.

FIG. 6 shows valve 16 in a released position with lever 18 and plunger 34 raised upwardly, and spring 38 extended. Stationary pinching pin 36 pinches tube 20 within hole 37, which is contained in plunger 34, as plunger 34 is raised.

Figure 7:
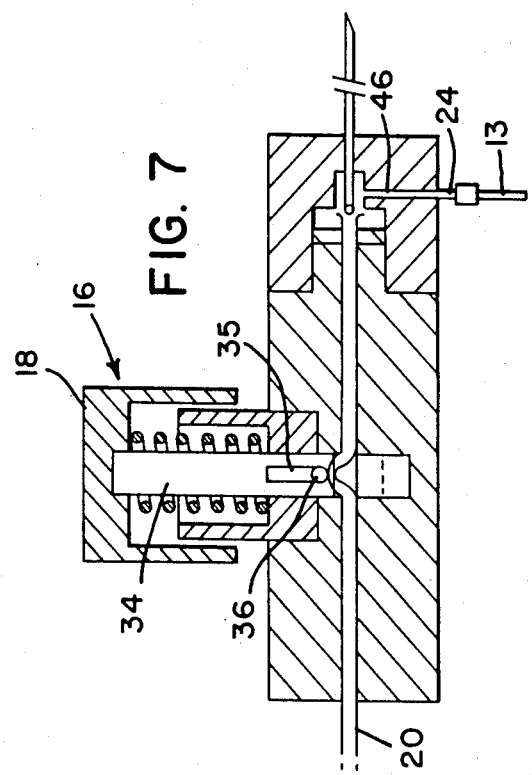
FIG. 7 shows a side sectional view of the apparatus from FIG. 5 with the valve in the "off" position.

FIG. 7 shows valve 16 similarly disposed as in FIG. 6. Lever 18 and plunger 34 are released with spring 38 not being compressed. Pinching pin 36 extends through slot 35 and pinches tubing 20 which extends through hole 37 (see FIG. 6).

Figure 8:
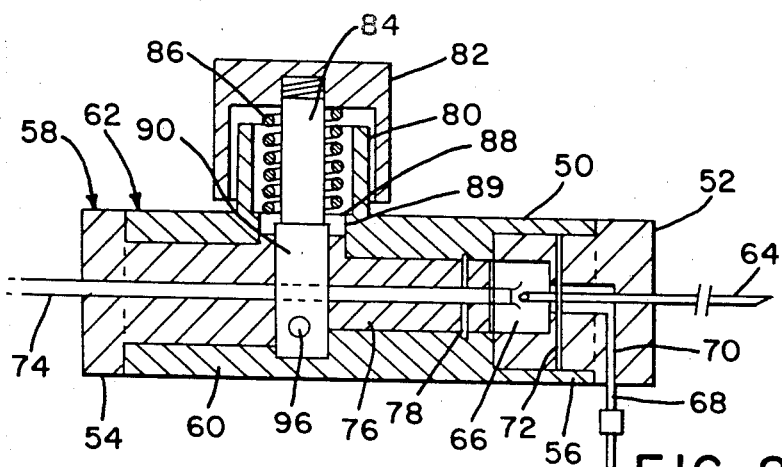
FIG. 8 shows a side sectional view of another embodiment of the apparatus in accordance with the present invention with the valve in the "on" position.
Figure 9:
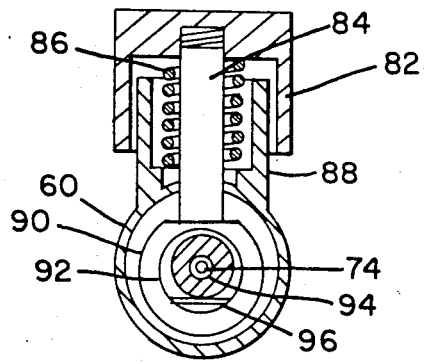
FIG. 9 is an end view of the embodiment illustrated in FIG. 8.
Figure 10:
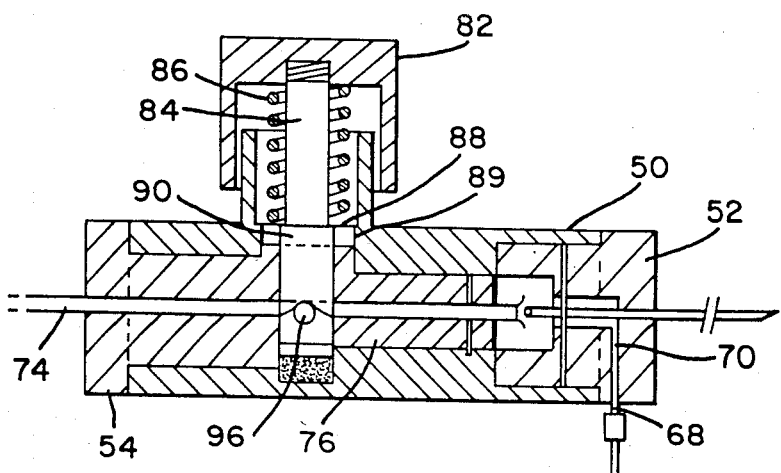
FIG. 10 is a side sectional view of the apparatus from FIG. 8 with the valve in the "off" position.

FIGS. 8 to 10 show another embodiment of an aspirating and flushing device, a portion of which is non-disposable, with the remainder being disposable. As best shown in FIGS. 8 and 9, housing 50 surrounds a portion of first body position 52 and second body portion 54.

Lip 56 on housing 50 surrounds first body portion 52 and is secured to housing 50 by O-ring 72. Lip 60 of housing 50 surrounds second body portion 54. Insertion of body 54 and extension 76 into housing 50 can be accomplished only when marker 58, is in line with marker 62, which marker 62 is a grooved line on housing 50. In addition, insertion and removal of body 54 and extension 76 can be performed only when lever 82 is fully depressed. First body portion 52 has a needle 64 extending outwardly from one end and a fluid flushing chamber 66 bored in the other end. Syringe portal 68 extends outwardly from a fluid flushing passageway 70 leading into flushing chamber 66. O-ring 72 provides a seal between lip 56 of housing 50 and first body portion 52.

Flexible tubing 74 extends through hole 94 in second body portion 54 and extension 76, and into flushing fluid chamber 66. Extension 76 extends through inner portion 92 of plunger head 90. The end of tubing 74 within fluid flushing chamber 66 surrounds the proximal end of needle 64 which also extends into flushing chamber 66. O-ring 78 provides a seal between housing 50 and extension 76 of body 54. Valve housing 80 surrounds spring 86 and washer 88 resides within housing 50. Shelf 89, on housing 80, supports washer 88, thereby supporting spring 86. Plunger 84 connects to lever 82 and has plunger head 90 connected thereto. Pinching pin 96 resides within plunger head 90.

FIG. 10 shows the valve of FIGS. 8 and 9 similarly disposed with the valve in the depressed position. Lever 82 and plunger 84 are in the downward position with spring 86 compressed against washer 88, which rests on shelf 89. Plunger head 90 is surrounded by housing 50 and in turn surrounds an inner portion 92 (see FIG. 9) of second body portion 54. Lever 82 and plunger 84 are in an upward position with spring 86 upwardly extended. Plunger head 90 is also pulled upward by plunger 84. Pinching pin 96 is raised upward and pinches tubing 74. Second body 54, extension 76 and first body 52 may be discarded after one-time use. There is no need for a locking pin as the unit is assembled immediately prior to use, therefore prolonged compression of tubing 74 is avoided.

Alternate embodiments of the present invention make the modified device ideally suited for use with the transvaginal ultrasound probe method of ovum (egg) retrieval procedures in IVF. The nature of the transvaginal method of ovum recovery prompted further improvements of the present invention consisting of placement of a collecting vessel onto the main body of the aspirating and flushing device and addition of a partially jacketed aspirating needle. Both embodiments have proven effective in the elimination of "dead-space," an inherent deficiency in prior art designs for transvaginal ovum recovery procedures.

Figure 11:
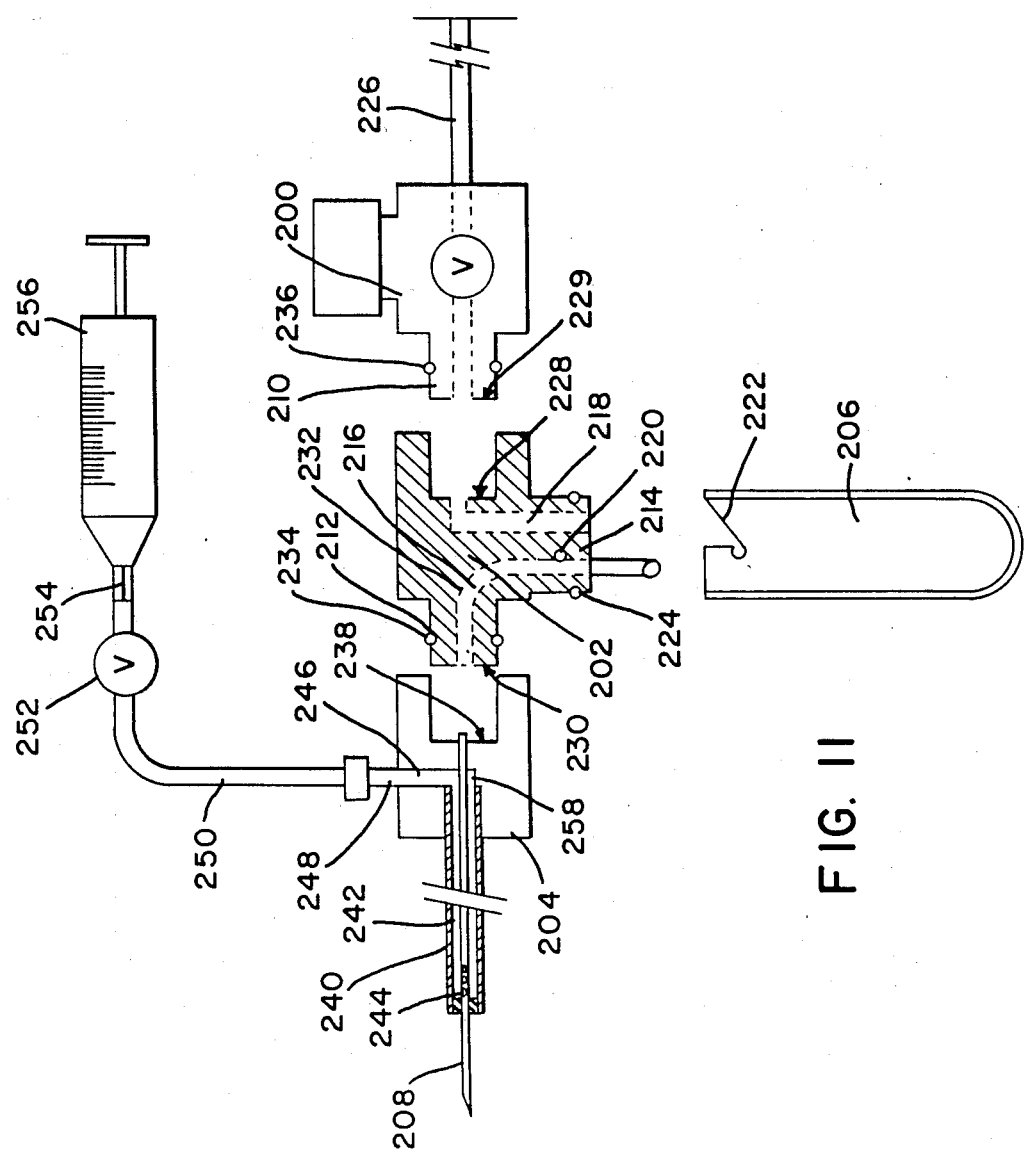
FIG. 11 is a schematic view of a system of apparatus for removing tissues, fluid and eggs in accordance with a further embodiment of the present invention.
Figure 12:
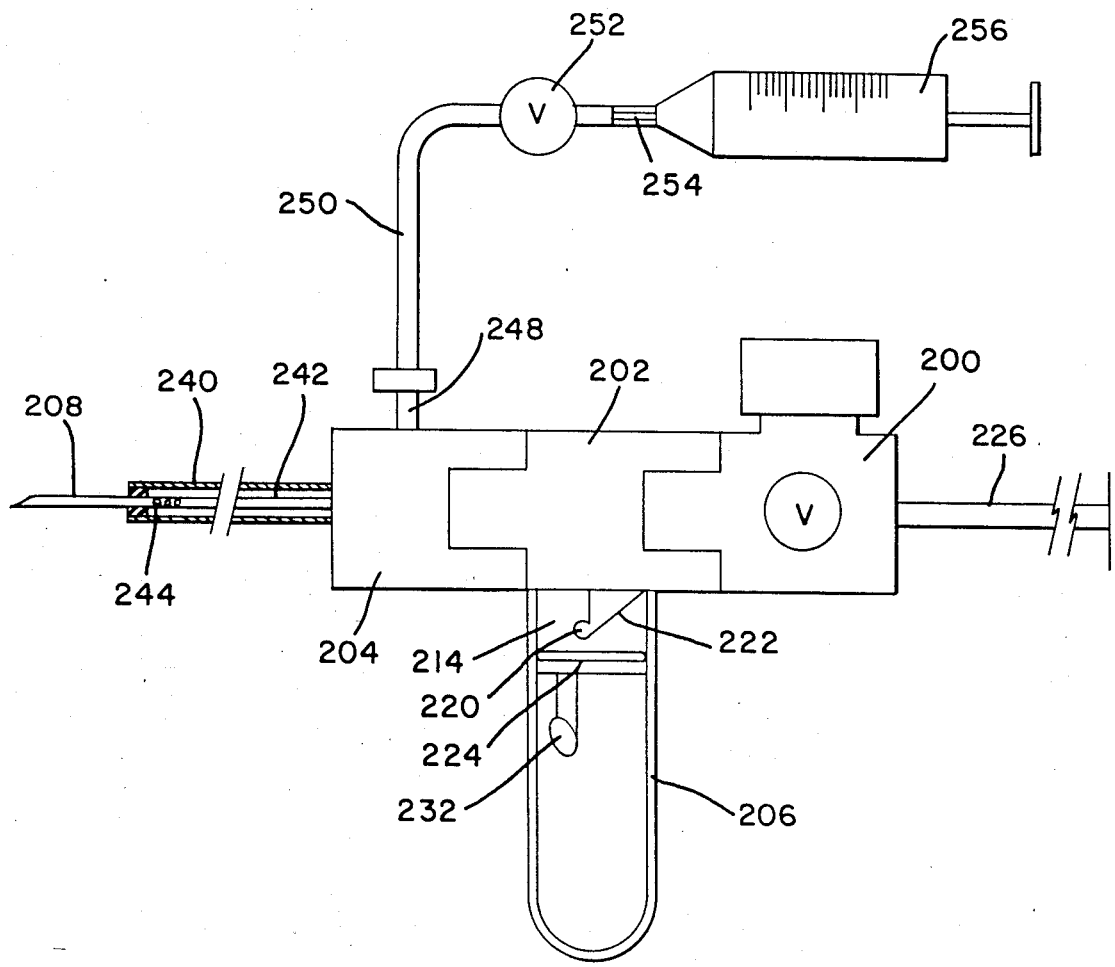
FIG. 12 shows the system from FIG. 11, broken apart for ease of understanding.

The main body of the aspirating and flushing device consists of three component parts which are interchangable and connected by the sealing effect of O-rings as best shown in FIGS. 11 and 12. Suction control valve assembly 200 remains essentially the same in design and function as second body 14 previously described in FIGS. 1 to 10. Coupling unit 202 is positioned between valve unit 200 and needle unit 204 provides a means for attaching collecting vessel 206 distal to valve assembly 200 and closer to a proximal portion of aspirating needle 208.

The proximal end of coupling unit 202 is designed to accept the insertion of extension 210, having an O-ring 236, which is an extended portion of valve assembly 200. The distal portion of coupling unit 202 contains an extension 212 which is essentially the same as that found on valve assembly 200, which inserts into a third body of the device, namely needle unit 204. In addition, coupling unit 202 has a cylindrical portion 214 extending downwardly therefrom to permit attachment of collecting vessel 206. Cylindrical portion 214 contains a locking pin 220 which is received by a notch 222 in collecting vessel 206. An O-ring 224 seals cylindrical portion 214 and collecting vessel 206.

Within coupling unit 202 there are two hollow passageways 216 and 218, wherein plastic tubing is preferably molded. The first of these passageways 218 begins at flat surface 228 of coupling unit 202 and extends therethrough. Passageway 218 further extends through cylindrical portion 214 and leads to collecting vessel 206. Second passageway 216 starts inside collecting vessel 206 and terminates at smooth surface 230 on extension 212. The proximal end of needle unit 204 is designed to admit extension 212, thereby permitting plastic tubing 232 within passageway 216 to loosely surround a proximal portion of needle 208 when needle unit 204 and coupling unit 202 are connected. O-ring 234 provides a seal therebetween.

Needle unit 204 has an aspirating needle 208 extending therefrom (preferably about 40 cm. in length), the proximal end of which is fixed into needle unit 204 and extends outwardly from needle unit 204 at flat surface 238 and further extends into tubing 232 in passageway 216. The proximal end (preferably about 30 cm.) of main aspirating needle 208 is enclosed with semi-rigid jacket 240. Jacket 240 is secured to the terminal portion of needle unit 204 and to aspirating needle 208, thereby creating an airtight space 242 between needle 208 and jacket 240. Needle 208 contains small fenestrations 244, preferably three fenestrations, which are located in the distal portion of needle 208 which is enclosed by jacket 240.

In addition, needle unit 204 contains a fluid passageway 246 and syringe portal 248 to which flexible tubing 250 is attached and contains an open-close valve 252 and fitting 254 for the placement of syringe 256. Syringe portal 248 extends into needle unit 204 by way of a hollow passageway 246 which terminates or is contiguous with flushing chamber 258.

Figure 13:
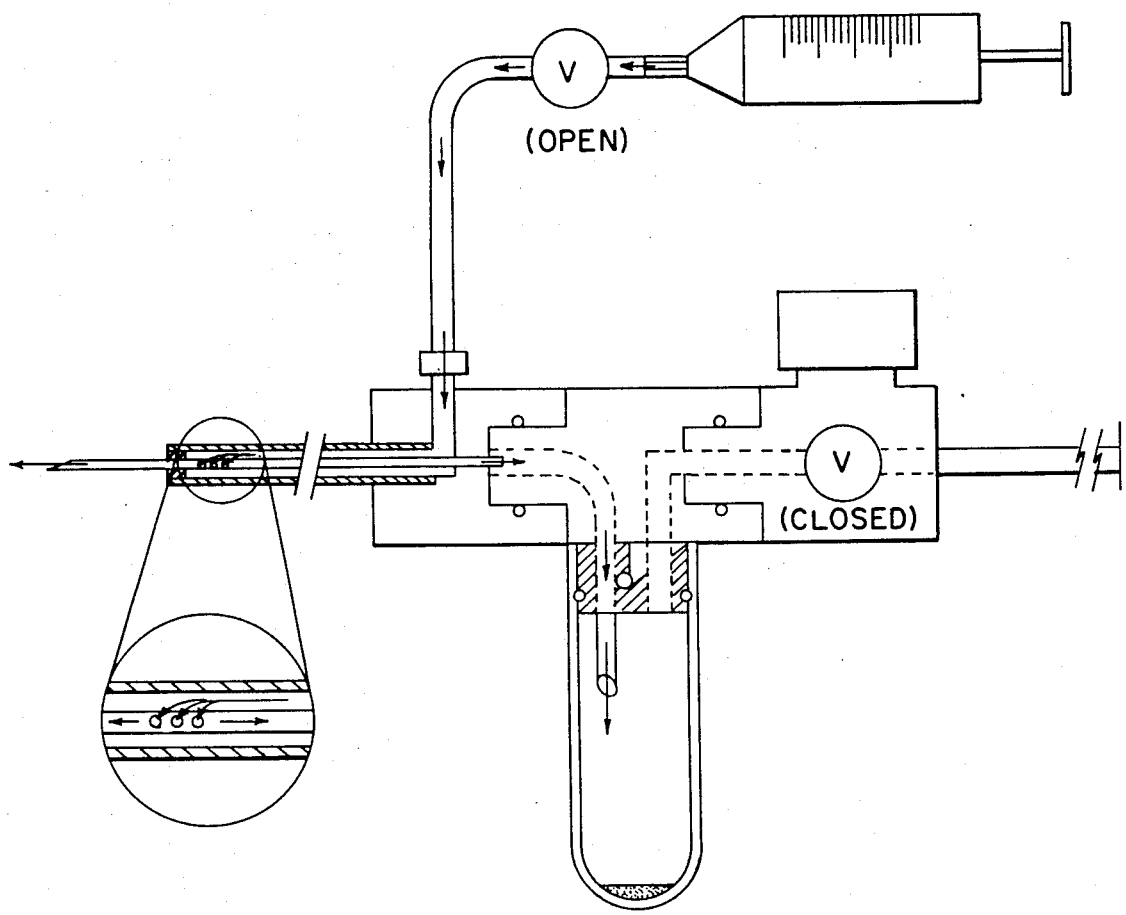
FIG. 13 shows the system from FIG. 11 in a "flushing" mode.
Figure 14:
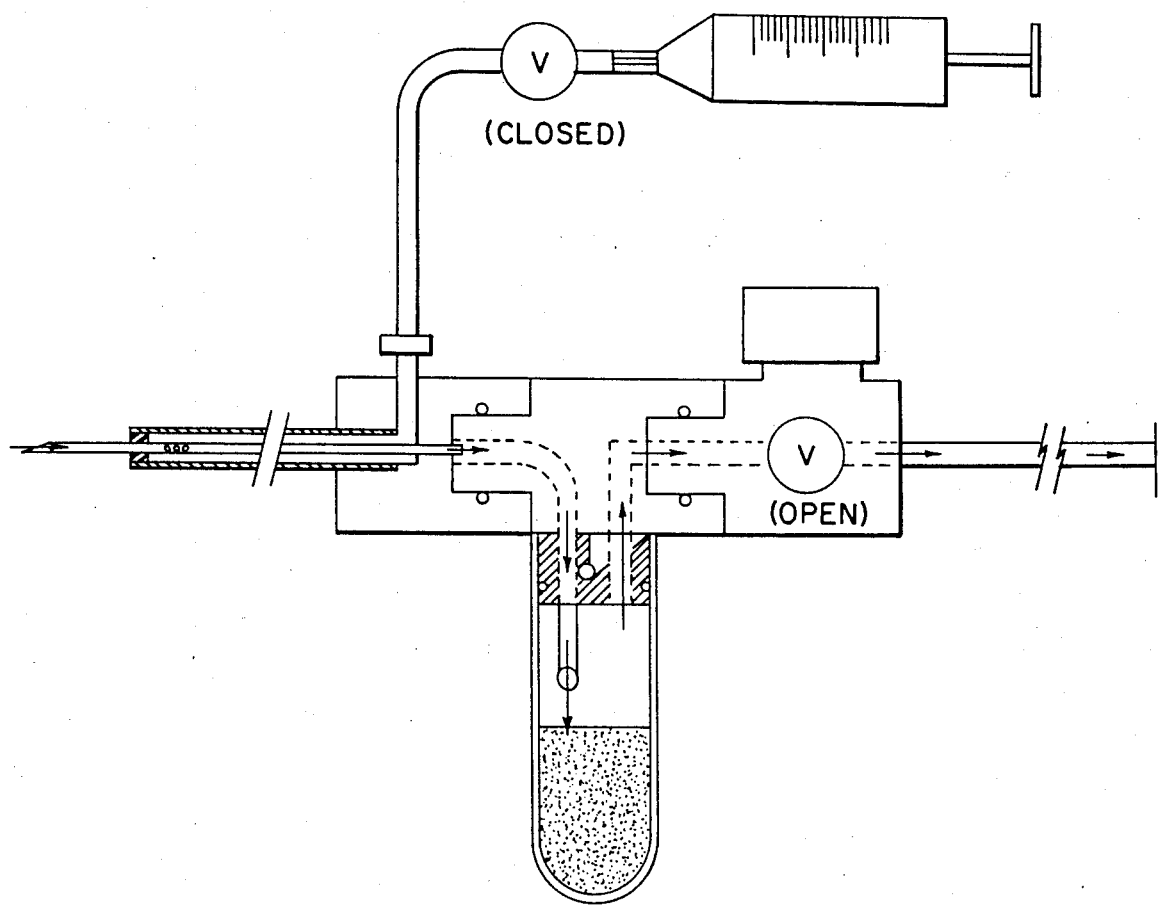
FIG. 14 shows the system from FIG. 11 in an "aspiration" mode.

Referring now to FIG. 13, when valve 200 is in the off position and collecting vessel 206 is locked by pin 220, flushing fluid may be injected from syringe 256 into tubing 250 if open-close switch 252 is open. Flushing solution then flows through tubing 250, flushing portal 248, passageway 246 and into flushing chamber 258 as shown by the arrows. Once flushing solution enters flushing chamber 258, it flows downwardly toward the terminal end of needle 208 in space 242 provided between needle 208 and jacket 240. It then enters needle 208 through fenestrations 244 and exits at the distal end of needle 208 onto the target area, also shown by the arrows. Referring now to FIG. 14, a portion of flushing solution will travel in a retrograde direction as shown by the arrows when valve 252 is closed and valve unit 200 is open until pressure resistance within the system is greater than that required to redistend the ovarian follicle. This amount of fluid is small and is a beneficial feature. Specifically, fluids and tissues flow into the distal end of needle 208, past fenestrations 244 and into the proximal end of needle 208. The fluids and tissues, preferably including an egg, flow into passageway 216, through cylindrical portion 214 and into collecting vessel 206. Because valve 252 is closed, the aspirate may not flow into fenestrations 244 and away from collecting vessel 206. Similarly, opening valve unit 200 permits vacuum suction to pull the aspirate into vessel 206. These improvements have virtually eliminated the deficiency of "dead-space" found in prior art devices, as well as preserving an optimum diameter for aspirating needle 208.

Figure 15C:
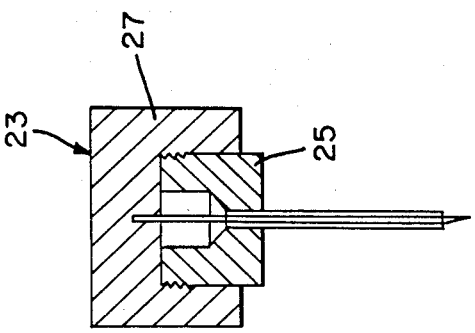
FIG. 15 is a side plan view of the valve portion of one embodiment of the apparatus along with side sectional views of an interchangable cannula means and a puncture needle, as utilized in accordance with the present invention.
Figure 15B:
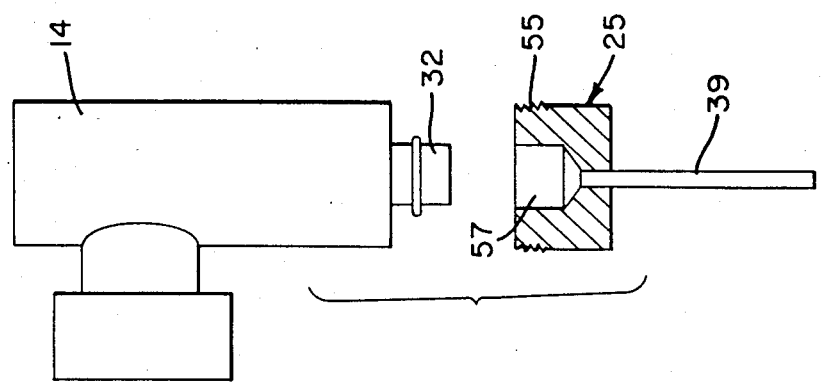
Figure 15A:
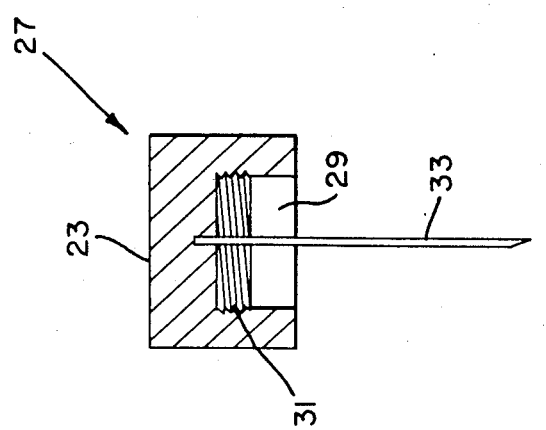

In FIG. 15A, trocar body portion 27 has a butt end 23 and a cannula body receiving end 29 with threads 31. Trocar 33 extends from trocar body portion 27 by way of cannula body receiving end 29. In FIG. 15B, second body portion 14 and extension 32 are positioned to receive cannula body portion 25. Cannula body portion 25 has threads 55 on the outside and a trocar body extension receiving space 57 on the inside. Cannula 39 extends therefrom. FIG. 15C shows cannula body portion 25 and trocar butt end 23 threaded together.

Device 10 can be employed in a wide variety of surgical situations and procedures where it is desirable to aspirate and/or flush tissue and/or fluids. It has been found that the present invention and its embodiments is particularly suited for surgical procedures involving IVF either alone or in combination with other devices. Hereinbelow, the apparatus of the present invention will be specifically explained based on the type of surgical procedure for which it has been found to be particularly useful. It should be recognized, however, that the apparatus utilized in accordance with the present invention, can be employed in other varied micro-type surgical procedures.

In the performance of the GIFT method of IVF, eggs are recovered by the usual laparoscopic technique, immediately inseminated and placed in the Fallopian Tube while the patient remains under anesthetic. Positioning of the delicate finger-like portion of the Fallopian Tube is critical in order to identify the tubal opening into which a fine catheter is introduced in order to deposit the sperm-egg mixture. An extension of the present invention shown in FIG. 15B, is useful as a grasping and holding device for delicate tissues simply by attaching body 14 into space 57 via extension 32. When suction is actuated by depressing lever 18, the vacuum created provides an efficient and atraumatic method for holding delicate structures.

The embodiment depicted in FIGS. 8 through 10, while providing the same efficient function as the disposable valve assembly 10, in intended to be partially disposable and partially re-usable after adequate cleansing and surgical sterilization. Specifically, it is preferred that housing 60 be reusable.

The present invention and embodiments provide an apparatus that is adaptable in either the laparoscopic or transvaginal ultrasound methods of IVF ovum recovery The laparoscopic procedure involves first introducing carbon dioxide gas into the abdominal cavity in order to provide operative room and visibility. This is typically done with the use of an insufflating needle which is made to pierce the abdominal walls in the area of the patient's navel. When adequate abdominal distension is achieved, the insufflation needle is removed and a laparoscope is inserted into the abdominal cavity through the same puncture site as the insufflation needle. The laparoscope, which contains a refined lens system and light source, enables the abdominal contents to be clearly viewed. The hollow cannula unit shown in FIG. 15C contains a sharp pointed stylet 33 and is thrust through the abdominal wall at an avascular area in the lower portion of the abdomen. When the stylet shown in FIG. 15A is removed, the cannula serves as a passageway for the aspirating and flushing device illustrated in FIG. 1 or can act as a suction device for grasping and holding delicate tissue as in the GIFT procedure. This is possible when body 14 is connected to 57 as illustrated in FIG. 15B.

When performing ordinary ovum recovery procedures laparoscopically, a third puncture is necessary in order to introduce a grasping forceps which is needed to hold the ovary in place when the needle penetrates the ovary. The port of entry for this third puncture is usually just above the bladder area in the midline. Before beginning this particular procedure, device 10 is first assembled as shown in FIG. 1 by connecting portion 14 and portion 12 containing needle 22. It should be noted that when the aspirating and flushing device is not in use or is packaged and/or stored, it is essential that lever 18 remain in the depressed position in order not to maintain plastic tubing 20 in a pinch position for long periods of time. This is accomplished by inserting pin 39 which secures lever 18 to housing 40, thereby securing the valve in the downward or open mode. Pin 39 is removed just prior to use of the device.

After inserting needle 22 into the patient's abdominal cavity through cannula 39, the surgeon locates a suitable egg-containing follicle on an ovary and, after stabilizing the ovary with the grasping forceps, proceeds to penetrate the follicle with aspirating needle 22. Simultaneous to this puncture the surgeon activates suction by depressing lever 18. With the activation of suction, the fluid contents of the ovarian follicle and human egg are sucked into needle 22 and passed directly and atraumatically into tubing 20 and into the collecting vessel 17. In the performance of laparoscopic ovum retrieval, collecting vessel 17 can be distant from the proximal end of the aspirating needle 22 without fear of "dead-space" because momentary removal of needle 22 from the follicle will permit carbon dioxide gas to direct the aspirated material to collecting vessel 17. If necessary, needle 22 can be gently reinserted into the point of entry of the follicle under direct laparoscopic vision.

Depending upon the size of the available conduit to the vacuum source, different sizes of flexible tubing 20 may be provided. Similarly the surgeon may desire different sizes of needles 22, cannulas 39 or trocars 33. Having separate body portions such as those alternatively illustrated allows for increased interchangability and for added flexibility of the invention.

Psychologically, it has been found that the preferred valve or "on-off" mechanism is one which actuates suction when depressed and terminates suction upon release. This requirement dictates against prior art designs since it is far easier to construct a valve which terminates flow when depressed and actuates flow upon release. In the present invention pinching pin 36 pinches tubing 20 before pressing, which prevents aspiration, as shown in FIG. 8. As the surgeon presses on lever 18, compression on tubing 20 is released as shown in FIG. 7. As stated previously, when suction is actuated, fluids and the egg are sucked into needle 22 and pass directly and atraumatically into tubing 20. This atraumatic passage is most critical because of the delicateness of the human egg in this instance, or because of the delicateness of body tissues in general. The novel construction of the present invention insures that the egg is removed and that aspirating and flushing device 10 permits atraumatic passage of the aspirate between the proximal end of needle 22 and the distal end of tubing 20. An important part of this construction is located within fluid flushing chamber 30 and requires that the terminal end of tubing 20 be flared as shown in FIGS. 5, 7, 8 and 10. The need for flaring typically arises upon the usage of a large gauge needle 22 as compared to the gauge of the flexible tubing 20. Smaller gauge needles 22 generally do not require flaring, although flaring does not impair the effectiveness of the device. It is important also that there is a very slight overlapping of needle 22 and tubing 20 which creates a "umbrella" effect. If there is no umbrella effect, as in the case with prior art devices, there is a tendency for the tissue and/or fluids to escape either temporarily or permanently into the fluid flushing chamber 30. Even if recovered after such an escape, any tissue or egg would be subjected to severe turbulence and possible physical damage.

When using the device for laparoscopic ovum retrieval, it is important that a space remain between the ends of tubing 20 and needle 22 despite the overlapping requirements. This space is needed in order for flushing fluid or irrigant to be introduced into needle 22. After the contents of the ovarian follicle are removed through aspiration, the follicle collapses and if the egg has not been retrieved in the aspirate, redistending of the ovarian follicle with a flushing solution becomes necessary in order to dislodge the egg for recovery. Such redistending is accomplished by introducing irrigant solution through needle 22 and back into the ovarian follicle without the need for removing needle 22.

In order to introduce a flushing solution or irrigant through needle 22 into the ovarian follicle, a syringe containing flushing fluid connects to flexible tubing 13 containing an "on-off" valve 100. Tubing 13 is connected to flushing portal 24 where it passes through passageway 46 into chamber 30 where fluid enters needle 22 and tubing 20. Flushing fluid then traverses the entire length of needle 22 and redistends the follicle. It is essential that during the flushing maneuver that tubing 20 be compressed by pinching pin 36 as shown in FIGS. 6, 7 and 10, thereby preventing any flow past plunger 34. Valve 100 is in the open position to permit introduction of flushing fluid into the system. When aspiration is to be performed valve 10 is in the depressed or open position, while valve 100 is in the closed position.

The aspirating and flushing device 10 designed for laparoscopic ovum recovery use is shown in FIG. 1 through 8 and is intended for one time use only. Body members are interchangable and remain secured by the sealing effect of the O-ring, although PVC plastic is preferred for a variety of reasons, including machinability, weight, cost and lack of toxicity.

I claim:

1. Apparatus for removing tissue and living organisms comprising:
    a first body having a hollow needle with distal and proximal end portions, said needle extending outwardly therefrom and extending into a chamber within said first body on the other end, said first body also having a syringe passageway connected to a jacket surrounding a proximal portion of said needle, said jacket being sealed against the needle at its distal end and providing a space connecting to a plurality of fenestrations in said needle for the introduction of flushing fluid into said needle;
    a second body fixable to said first body and having a first bore extending from an end portion of said second body to a side portion of said second body, said side portion having means for connection to a collection vessel, said second body having a second bore extending from said side portion to a chamber within said second body on the other end;
    a third body fixable to said second body and having a bore which contains flexible tubing, said tubing being connectable to vacuum means on one end and extending outwardly from an end portion of said third body and into the chamber of said second body on a second end; and
    valve means extending from said third body and being in releasable engagement with said tubing for decompressing or compressing said tubing for actuating on-off suction action through said needle, said suction action occurring upon application of pressure to said valve.

2. Apparatus as defined in claim 1 wherein sealing means are provided on said end portions of said second and third bodies and said side portion of said second body.

3. Apparatus as defined in claim 1 wherein said needle opening into said chamber extends outwardly and into said chamber, and said flexible tubing extends outwardly from said end portion of said second body and extends over and surrounds a portion of said needle extending into said chamber.

4. Apparatus as defined in claim 1 wherein said flexible tubing extending outwardly from said end portion of the second body is flared at the end and is free of contact with said needle.

5. Apparatus as defined in claim 1 wherein said valve means comprises:
    a valve seat, having a hole extending therethrough;
    spring means connected to said valve seat;
    a switch portion adjacent said spring means for urging said spring means against said valve seat;
    a plunger extending from said switch portion through said valve seat hole and into said second body, said plunger having an elongated first slot extending therethrough and being substantially perpendicular to said flexible tubing and a second slot extending therethrough and being substantially perpendicular to said first slot, with said flexible tube passing therethrough; and
    a rigid pinching bar extending through said first slot and fixedly mounted in said second body, whereby said tubing is pinched against the bottom of said pinching bar upon release of said plunger which pulls said tubing within said second slot toward said pinching bar.

6. Apparatus as defined in claim 5 wherein the bottom of said valve seat is beveled to prevent cutting of said tubing.

7. Apparatus as defined in claim 5 wherein said ring further comprises a rigid bar extending across a lower portion of the inside of said ring, wherein said bar pinches said tubing upon release of said switch portion.

8. Apparatus as defined in claim 1 wherein said bores contain flexible tubing.

9. Apparatus as defined in claim 1 wherein said needle contains three of said fenestrations.

10. Apparatus as defined in claim 1 wherein said second body has a locking pin in said side portion to lock said collecting vessel.

* * * * *